(12) United States Patent
Arikawa et al.

(10) Patent No.: US 10,233,468 B2
(45) Date of Patent: Mar. 19, 2019

(54) HIGH MOLECULAR WEIGHT PHA-PRODUCING MICROBE AND METHOD OF PRODUCING HIGH MOLECULAR WEIGHT PHA USING SAME

(71) Applicant: KANEKA CORPORATION, Kita-ku (JP)

(72) Inventors: Hisashi Arikawa, Takasago (JP); Shunsuke Sato, Takasago (JP); Keiji Matsumoto, Takasago (JP)

(73) Assignee: KANEKA CORPORATION, Kita-ku (JP)

( * ) Notice: Subject to any disclaimer, the term of this patent is extended or adjusted under 35 U.S.C. 154(b) by 0 days.

(21) Appl. No.: 14/437,672

(22) PCT Filed: Oct. 22, 2013

(86) PCT No.: PCT/JP2013/078520
§ 371 (c)(1),
(2) Date: Apr. 22, 2015

(87) PCT Pub. No.: WO2014/065253
PCT Pub. Date: May 1, 2014

(65) Prior Publication Data
US 2016/0237462 A1    Aug. 18, 2016

(30) Foreign Application Priority Data

Oct. 22, 2012 (JP) ................. 2012-232694
Oct. 22, 2012 (JP) ................. 2012-232695

(51) Int. Cl.
| | |
|---|---|
| *C12P 7/62* | (2006.01) |
| *C12N 15/74* | (2006.01) |
| *C12N 9/18* | (2006.01) |

(52) U.S. Cl.
CPC .............. *C12P 7/625* (2013.01); *C12N 9/18* (2013.01); *C12N 15/74* (2013.01)

(58) Field of Classification Search
None
See application file for complete search history.

(56) References Cited

U.S. PATENT DOCUMENTS

| | | | |
|---|---|---|---|
| 5,811,272 A | 9/1998 | Snell et al. | |
| 5,917,002 A | 6/1999 | Doi et al. | |
| 6,593,116 B1 | 7/2003 | Huisman et al. | |
| 7,384,766 B2 * | 6/2008 | Maruyama | C12N 15/52 435/252.3 |
| 9,175,317 B2 * | 11/2015 | Sato | C12N 9/1029 |
| 2005/0239998 A1 | 10/2005 | Kinoshita et al. | |
| 2008/0038801 A1 | 2/2008 | Maruyama | |
| 2009/0130731 A1 | 5/2009 | Maruyama | |

FOREIGN PATENT DOCUMENTS

| | | |
|---|---|---|
| EP | 1 739 182 A1 | 1/2007 |
| JP | 10-176070 A | 6/1998 |
| JP | 2001-275675 A | 10/2001 |
| JP | 2007-228894 A | 9/2007 |
| WO | WO 2005/085460 A1 | 9/2005 |
| WO | WO 2006/101176 A1 | 9/2006 |
| WO | WO 2012/071657 A1 | 6/2012 |
| WO | WO 2102/102371 * | 8/2012 |
| WO | WO 2013/153180 A1 | 10/2013 |

OTHER PUBLICATIONS

Saegusa et al., J. of Bacteriology vol. 183, No. 1, pp. 94-100, Jan. 2001.*
Ngo et al. in The Protein Folding Problem and Tertiary Structure Prediction, 1994, Merz et al. (ed.), Birkhauser, Boston, MA, pp. 433 and 492-495.*
Vandamme and Coenye, International Journal of Systematic Microbiolgy, vol. 54, pp. 2285-2289, 2004.*
Lei Cai, et al., "Enhanced production of medium-chain-length polyhydroxyalkanoates (PHA) by PHA depolymerase knockout mutant of *Pseudomonas putida* KT2442" Bioresource Technology, vol. 100, 2009, pp. 2265-2270.
Laura Isabel de Eugenio, et al., "The turnover of medium-chain-length polyhydroxyalkanoates in *Pseudomonas putida* KT2442 and the fundamental role of PhaZ depolymerase for the metabolic balance" Environmental Microbiology, vol. 12, No. 1, 2010, pp. 207-221.
Ken'ichiro Matsumoto, et al., "Chimeric Enzyme Composed of Polyhydroxyalkanoate (PHA) Synthases from *Ralstonia eutrophy* and *Aeromonas caviae* Enhances Production of PHAs in Recombinant *Escherichia coli*" Biomacromolecules, vol. 10, No. 4, XP002722989, 2009, pp. 682-685.
Xue Gao, et al., "Production of copolyesters of 3-hydroxybutyrate and medium-chain-length 3-hydroxyalkanoates by *E. coli* containing an optimized PHA synthase gene" Microbial Cell Factories, vol. 11:130, 2012, pp. 1-10.

(Continued)

*Primary Examiner* — Richard G Hutson
(74) *Attorney, Agent, or Firm* — Oblon, McClelland, Maier & Neustadt, L.L.P.

(57) ABSTRACT

An object of the present invention is to provide a microorganism strain that accumulates a high molecular weight PHA, and a PHA production method using the microorganism. The present invention provides a method for producing a PHA copolymer, which includes culturing a microorganism, wherein at least a portion of either of the following genes (a) and (b) of the microorganism has been altered by substitution, deletion, insertion, and/or addition to reduce or eliminate the activity of a PHA degrading enzyme encoded by the gene: (a) a PHA degrading enzyme gene encoding the amino acid sequence of SEQ ID NO:2 in the sequence listing; and (b) a gene encoding a polypeptide having at least 85% sequence identity to the amino acid sequence of SEQ ID NO:2 in the sequence listing and having PHA degrading enzyme activity.

17 Claims, No Drawings
Specification includes a Sequence Listing.

(56) References Cited

OTHER PUBLICATIONS

Tae-Kwon Kim, et al., "Metabolic Engineering and Characterization of phaC1 and phaC2 Genes from *Pseudomonas putida* KCTC1639 for Overproduction of Medium-Chain-Length Polyhydroxyalkanoate" Biotechnology Progress, vol. 22, No. 6, 2006, pp. 1541-1546.

Gustavo Graciano Fonseca, et al., "Use of Vegetable Oils as Substrates for Medium-chain-length Polyhydroxyalkanoates Production by Recombinant *Escherichia coli*" Biotechnology, vol. 5, No. 3, 2006, pp. 277-279 and Cover Page.

International Search Report dated Dec. 17, 2013 in PCT/JP2013/078520.

International Preliminary Report on Patentability and Written Opinion dated Apr. 28, 2015 in PCT/JP2013/078520 (English Translation only).

Abe, T., et al., "Properties of a Novel Intracellular Poly(3-hydroxybutyrate) Depolymerase with High Specific Activity (PhaZd) in *Wautersia eutropha* H16", J. Bacteriol., 2005, vol. 187, No. 20, pp. 6982-6990.

York, G. M., et al., "*Ralstonia eutropha* H16 Encodes Two and Possibly Three Intracellular Poly[D-(-)-3-hydroxybutyrate] Depolymerase Genes", J. Bacteriol., 2003, vol. 185, No. 13, pp. 3788-3794.

Pohlmann, A. et al., "Genome Sequence of the Bioplastic-producing "Knallgas" Bacterium *Ralstonia eutropha* H16", Nat. Biotechnol., 2006, vol. 24, No. 10, 6 pages.

S. Kusaka et al., "Molecular Mass of Poly[(R )-3-hydroxybutyric acid] Produced in a Recombinant *Escherichia Coli*", Appl. Microbiol. Biotechnol., (1997), 47, pp. 140-143.

Satoshi Kusaka et al., "Properties and Biodegradability of Ultra-high-molecular-weight Poly[(R)-3-hydroxybutyrate] Produced by a Recombinant *Escherichia coli*", International Journal of Biological Macromolecules, 25,(1999), pp. 87-94.

Katja Peplinski et al., "Genome-wide Transcriptome Analyses of the 'Knallgas' Bacterium *Ralstonia eutropha* H16 with Regard to Polyhydroxyalkanoate Metabolism", Microbiology, (2010), 156, pp. 2136-2152.

Hiroe et al, "Rearrangement of Gene Order in the phaCAB Operon Leads to Effective Production of Ultrahigh-Molecular-Weight . . . ", *Applied and Environmental Microbiology*, Feb. 2017, pp. 3177-3184.

Kawaguchi et al, "Kinetics and Mechanism of Synthesis and Degradation of Poly(3-hydroxybutyrate) in *Alcaligenes eutrophus*", *Macromolecules*, 1992, vol. 25, pp. 2324-2329.

Madden et al, "Chain termination in polyhydroxyalkanoate synthesis: involvement of exogenous hydroxy-compounds as chain transfer agents", *International Journal of Biological Macromolecules*, 1999, vol. 25, pp. 43-53.

Shimizu et al, "Kinetic Study of Poly-D(-) -3-Hydroxybulyric Acid (PHB) Production and Its Molecular Weight Distribution Control in a Fed-Batch Culture of *Alcaligenes eutrophus*", *Journal of Fermentation and Bioengineering*, 1993, vol. 6, pp. 465-469.

\* cited by examiner

SEQUENCE LISTING

<160> NUMBER OF SEQ ID NOS: 19

<210> SEQ ID NO 1
<211> LENGTH: 1089
<212> TYPE: DNA
<213> ORGANISM: Cupriavidus necator

<400> SEQUENCE: 1

```
atgaccaaaa gctttgccgc tgactggcac gcgcagatcc ggcgactgag ccgtgcgcaa      60
gcccgcacgg aagcccaggt gaagtcctgg ctggaccgcg tggattcgct taatccgctc     120
acgccggctc ggcctgaccg cccgccgggc aaggtccggc ccgccggcc agcacccgcg      180
ccgggttccc tgcccggtac ctggcaggcg cacaggctgc gcctggcgcc gctgccgggc     240
gaactggtgc cgcaactctc gtatcacctc tacataccgt ccaaggccca tcgcggcccg     300
ttgccggtgg tggtggtgct gcatggctgt cgccagacgc cggatgacct gtcggccggc     360
acccgcatga atgcgctggc cgagcgcgag ggatttatcg tggcctaccc gcaacagccc     420
ttgcggcgcc aggtgcagcg ctgctggcag tggttcgacc tgggcgccgc tgaggcgga     480
cgcgaggcgc aggcggtggc cgcgctgatc gatgcgctgg ctgcgcgcca cgacgtcgc      540
gagcgcgaga tctacctggc cggcatgtcc gccggcgcgg ccatggccgc ggtggtggcg     600
ttgcgctacc cgggcaaggt ggcggccgcg cgcgctgcatt ccggcgtggt catcggcgcc    660
gccgacaacc cgcgcgccgg cctgcgggcc atgcagcaag gctcggcggc cgatccgtca     720
tggctgctgg atgccgccgg cgtgacgccg ggcggtcccg agatgccgc gctggtgatc     780
cacggcctgg ccgacgacgc ggtccatccg gtcaatggcc gtctgctggc gcggcagttc     840
ctggcttaca acggcctgga agaccggctc gccggtgcgc ccgcgcagtc cggcccggag     900
gacgaagcgc cgggccggtc tcatgaatac cgcttcggcc gctggcgccg cgacctggtc     960
acgctggtgg aagtggaggg cttgggccac gcctggagcg gcggcgatgc cagctatggc    1020
taccacagcg atatcggccc ggatgccagc acgatgatgt ggcagttctt cagccagcac    1080
cgccgttga                                                            1089
```

<210> SEQ ID NO 2
<211> LENGTH: 362
<212> TYPE: PRT
<213> ORGANISM: Cupriavidus necator

<400> SEQUENCE: 2

Met Thr Lys Ser Phe Ala Ala Asp Trp His Ala Gln Ile Arg Arg Leu
1               5                   10                  15

Ser Arg Ala Gln Ala Arg Thr Glu Ala Gln Val Lys Ser Trp Leu Asp
            20                  25                  30

Arg Val Asp Ser Leu Asn Pro Leu Thr Pro Ala Arg Pro Asp Arg Pro
                35                  40                  45

Pro Gly Lys Val Arg Pro Ala Arg Pro Ala Pro Gly Ser Leu
 50                  55                  60

Pro Gly Thr Trp Gln Ala His Arg Leu Arg Leu Ala Pro Leu Pro Gly
 65                  70                  75                  80

Glu Leu Val Pro Gln Leu Ser Tyr His Leu Tyr Ile Pro Ser Lys Ala
                85                  90                  95

His Arg Gly Pro Leu Pro Val Val Val Leu His Gly Cys Arg Gln
                100                 105                 110

Thr Pro Asp Asp Leu Ser Ala Gly Thr Arg Met Asn Ala Leu Ala Glu
                115                 120                 125

Arg Glu Gly Phe Ile Val Ala Tyr Pro Gln Gln Pro Leu Arg Arg Gln
 130                 135                 140

Val Gln Arg Cys Trp Gln Trp Phe Asp Leu Gly Ala Ala Glu Gly Gly
145                 150                 155                 160

Arg Glu Ala Gln Ala Val Ala Ala Leu Ile Asp Ala Leu Ala Ala Arg
                165                 170                 175

His Asp Val Arg Glu Arg Glu Ile Tyr Leu Ala Gly Met Ser Ala Gly
                180                 185                 190

Ala Ala Met Ala Ala Val Val Ala Leu Arg Tyr Pro Gly Lys Val Ala
                195                 200                 205

Ala Ala Leu His Ser Gly Val Val Ile Gly Ala Ala Asp Asn Pro
                210                 215                 220

Arg Ala Gly Leu Arg Ala Met Gln Gln Gly Ser Ala Ala Asp Pro Ser
225                 230                 235                 240

Trp Leu Leu Asp Ala Ala Gly Val Thr Pro Gly Gly Pro Glu Met Pro
                245                 250                 255

Ala Leu Val Ile His Gly Leu Ala Asp Asp Ala Val His Pro Val Asn
                260                 265                 270

Gly Arg Leu Leu Ala Arg Gln Phe Leu Ala Tyr Asn Gly Leu Glu Asp
                275                 280                 285

Arg Leu Ala Gly Ala Pro Ala Gln Ser Gly Pro Glu Asp Glu Ala Pro
290                 295                 300

Gly Arg Ser His Glu Tyr Arg Phe Gly Arg Trp Arg Arg Asp Leu Val
305                 310                 315                 320

Thr Leu Val Glu Val Glu Gly Leu Gly His Ala Trp Ser Gly Gly Asp
                325                 330                 335

Ala Ser Tyr Gly Tyr His Ser Asp Ile Gly Pro Asp Ala Ser Thr Met
                340                 345                 350

Met Trp Gln Phe Phe Ser Gln His Arg Arg
                355                 360

<210> SEQ ID NO 3
<211> LENGTH: 32
<212> TYPE: DNA
<213> ORGANISM: Artificial
<220> FEATURE:
<223> OTHER INFORMATION: synthetic primer1

<400> SEQUENCE: 3
gcgcatttaa atccggacct tcgtgcggct ca                                  32

<210> SEQ ID NO 4
<211> LENGTH: 20
<212> TYPE: DNA

```
<213> ORGANISM: Artificial
<220> FEATURE:
<223> OTHER INFORMATION: synthetic primer2

<400> SEQUENCE: 4
gaggactcct gatcgtgtga                                               20

<210> SEQ ID NO 5
<211> LENGTH: 40
<212> TYPE: DNA
<213> ORGANISM: Artificial
<220> FEATURE:
<223> OTHER INFORMATION: synthetic primer3

<400> SEQUENCE: 5
tcacacgatc aggagtcctc agtcgggcag caccaatgcg                         40

<210> SEQ ID NO 6
<211> LENGTH: 32
<212> TYPE: DNA
<213> ORGANISM: Artificial
<220> FEATURE:
<223> OTHER INFORMATION: synthetic primer4

<400> SEQUENCE: 6
gcgcatttaa atcgccacgc tgtgcctgac ga                                 32

<210> SEQ ID NO 7
<211> LENGTH: 34
<212> TYPE: DNA
<213> ORGANISM: Artificial
<220> FEATURE:
<223> OTHER INFORMATION: synthetic primer5

<400> SEQUENCE: 7
gcgcgcattt aaatcatggc atctacgccg tcgg                               34

<210> SEQ ID NO 8
<211> LENGTH: 20
<212> TYPE: DNA
<213> ORGANISM: Artificial
<220> FEATURE:
<223> OTHER INFORMATION: synthetic primer6

<400> SEQUENCE: 8 gcctttctg cctgggtcta                                                20

<210> SEQ ID NO 9
<211> LENGTH: 40
<212> TYPE: DNA
<213> ORGANISM: Artificial
<220> FEATURE:
<223> OTHER INFORMATION: synthetic primer7

<400> SEQUENCE: 9
tagacccagg cagaaaaggc gaaaacgccc gcgattgcgg                         40

<210> SEQ ID NO 10
<211> LENGTH: 34
<212> TYPE: DNA
<213> ORGANISM: Artificial
<220> FEATURE:
<223> OTHER INFORMATION: synthetic primer8

<400> SEQUENCE: 10
gcgcgcattt aaatacgctg gcgcgtttcg tctg                               34
```

<210> SEQ ID NO 11
<211> LENGTH: 32
<212> TYPE: DNA
<213> ORGANISM: Artificial
<220> FEATURE:
<223> OTHER INFORMATION: synthetic primer9

<400> SEQUENCE: 11
aaatagattt aaatgggaca gcagcaggat tt                          32

<210> SEQ ID NO 12
<211> LENGTH: 38
<212> TYPE: DNA
<213> ORGANISM: Artificial
<220> FEATURE:
<223> OTHER INFORMATION: synthetic primer10

<400> SEQUENCE: 12
gctggcggct gccgggggct cggtccccgc tattctgg                    38

<210> SEQ ID NO 13
<211> LENGTH: 38
<212> TYPE: DNA
<213> ORGANISM: Artificial
<220> FEATURE:
<223> OTHER INFORMATION: synthetic primer11

<400> SEQUENCE: 13
ccagaatagc ggggaccgag cccccggcag ccgccagc                    38

<210> SEQ ID NO 14
<211> LENGTH: 33
<212> TYPE: DNA
<213> ORGANISM: Artificial
<220> FEATURE:
<223> OTHER INFORMATION: synthetic primer12

<400> SEQUENCE: 14
aaatagattt aaatacaaag gcaaagggt agc                          33

<210> SEQ ID NO 15
<211> LENGTH: 594
<212> TYPE: PRT
<213> ORGANISM: Aeromonas caviae

<400> SEQUENCE: 15

Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
    50                  55                  60

Trp Gln Asp Gln Leu Lys Leu Met Gln His Thr Leu Leu Lys Ser Ala
65                  70                  75                  80

Gly Gln Pro Ser Glu Pro Val Ile Thr Pro Glu Arg Ser Asp Arg Arg
                85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala

-continued

```
            115                 120                 125
Leu Glu Gly Val Pro Gln Lys Ser Arg Glu Arg Leu Arg Phe Phe Thr
130                 135                 140

Arg Gln Tyr Val Ser Ala Met Ala Pro Ser Asn Phe Leu Ala Thr Asn
145                 150                 155                 160

Pro Glu Leu Leu Lys Leu Thr Leu Glu Ser Gly Gly Gln Asn Leu Val
                    165                 170                 175

Arg Gly Leu Ala Leu Leu Ala Glu Asp Leu Glu Arg Ser Ala Asp Gln
                180                 185                 190

Leu Asn Ile Arg Leu Thr Asp Glu Ser Ala Phe Glu Leu Gly Arg Asp
                195                 200                 205

Leu Ala Leu Thr Pro Gly Arg Val Val Gln Arg Thr Glu Leu Tyr Glu
210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                    245                 250                 255

Pro Gln Asn Ser Leu Val Ala Trp Leu Val Ala Gln Gly Gln Thr Val
                260                 265                 270

Phe Met Ile Ser Trp Arg Asn Pro Gly Val Ala Gln Ala Gln Ile Asp
                275                 280                 285

Leu Asp Asp Tyr Val Val Asp Gly Val Ile Ala Ala Leu Asp Gly Val
290                 295                 300

Glu Ala Ala Thr Gly Glu Arg Glu Val His Gly Ile Gly Tyr Cys Ile
305                 310                 315                 320

Gly Gly Thr Ala Leu Ser Leu Ala Met Gly Trp Leu Ala Ala Arg Arg
                    325                 330                 335

Gln Lys Gln Arg Val Arg Thr Ala Thr Leu Phe Thr Thr Leu Leu Asp
                340                 345                 350

Phe Ser Gln Pro Gly Glu Leu Gly Ile Phe Ile His Glu Pro Ile Ile
                355                 360                 365

Ala Ala Leu Glu Ala Gln Asn Glu Ala Lys Gly Ile Met Asp Gly Arg
370                 375                 380

Gln Leu Ala Val Ser Phe Ser Leu Leu Arg Glu Asn Ser Leu Tyr Trp
385                 390                 395                 400

Asn Tyr Tyr Ile Asp Ser Tyr Leu Lys Gly Gln Ser Pro Val Ala Phe
                    405                 410                 415

Asp Leu Leu His Trp Asn Ser Asp Ser Thr Asn Val Ala Gly Lys Thr
                420                 425                 430

His Asn Ser Leu Leu Arg Arg Leu Tyr Leu Glu Asn Gln Leu Val Lys
                435                 440                 445

Gly Glu Leu Lys Ile Arg Asn Thr Arg Ile Asp Leu Gly Lys Val Lys
                450                 455                 460

Thr Pro Val Leu Leu Val Ser Ala Val Asp Asp His Ile Ala Leu Trp
465                 470                 475                 480

Gln Gly Thr Trp Gln Gly Met Lys Leu Phe Gly Gly Glu Gln Arg Phe
                    485                 490                 495

Leu Leu Ala Glu Ser Gly His Ile Ala Gly Ile Asn Pro Pro Ala
                500                 505                 510

Ala Asn Lys Tyr Gly Phe Trp His Asn Gly Ala Glu Ala Glu Ser Pro
                515                 520                 525

Glu Ser Trp Leu Ala Gly Ala Thr His Gln Gly Gly Ser Trp Trp Pro
530                 535                 540
```

Glu Met Met Gly Phe Ile Gln Asn Arg Asp Glu Gly Ser Glu Pro Val
545                 550                 555                 560

Pro Ala Arg Val Pro Glu Glu Gly Leu Ala Pro Ala Pro Gly His Tyr
            565                 570                 575

Val Lys Val Arg Leu Asn Pro Val Phe Ala Cys Pro Thr Glu Glu Asp
        580                 585                 590

Ala Ala

<210> SEQ ID NO 16
<211> LENGTH: 1260
<212> TYPE: DNA
<213> ORGANISM: Cupriavidus necator

<400> SEQUENCE: 16

```
atgctctacc aattgcatga gttccagcgc tcgatcctgc acccgctgac cgcgtgggcc      60
caggcgaccg ccaagacctt caccaacccc ctcagcccgc tctcgctggt tcccggcgca     120
ccccgcctgg ctgccggcta tgaactgctg taccggctcg caaggaata cgaaaagccg      180
gcattcgaca tcaagtcggt gcgctccaac gggcgcgaca tccccatcgt cgagcagacc     240
gtgcttgaaa agccgttctg caagctggtg cgcttcaagc gctatgccga cgacccggag     300
accatcaagc tgctcaagga tgagccggtg gtgctggtgg ccgcgccgct gtcgggccac     360
catgccacgc tgctgcgcga cacggtgcgc acgctgctgc aggaccacaa ggtctacgtc     420
accgactgga tcgacgcacg catggtgccg gtcgaggaag gcgcgttcca cctgtcggac     480
tacatctact acatccagga attcatccgc catatcggcg ccgagaacct gcatgtgatc     540
tcggtatgcc agcccaccgt gccggtgctg gccgcgatct cgctgatggc ctcggccggc     600
gagaagacgc cgcgcaccat gaccatgatg ggcggcccga tcgacgcccg caagagcccc     660
accgcggtca actcgctggc gaccaacaag tcgttcgagt ggttcgagaa caacgtcatc     720
tacaccgtgc cggccaacta ccccggccac ggccgccgcg tctacccggg cttttttgcag   780
catgccggtt tcgtggcgat gaacccggac cggcacctttt cctcgcacta tgacttctac    840
ctgagcctgg tcgagggcga tgcggatgac gccgaagccc acgtgcgctt ctacgacgaa    900
tacaacgcgg tgctcgacat ggccgccgag tactacctcg acaccatccg cgaggtgttc    960
caggaattcc gcctggccaa cggcacctgg gccatcgacg gcaatccggt gcggccgcag    1020
gacatcaaga gcaccgcgct gatgaccgtc gagggcgaac tggacgacat ctcgggcgcg    1080
ggccagaccg ccgcggcgca cgacctgtgc gccggcatcc cgaaaatccg caagcagcac    1140
ctgaacgcgg cacactgcgg ccactacggc atcttctcgg gccggcgctg gcgcgaagag    1200
atctacccgc agctgcgcga ctttatccgc aagtaccacc aggcctcggc caccaggtaa    1260
```

<210> SEQ ID NO 17
<211> LENGTH: 419
<212> TYPE: PRT
<213> ORGANISM: Cupriavidus necator

<400> SEQUENCE: 17

Met Leu Tyr Gln Leu His Glu Phe Gln Arg Ser Ile Leu His Pro Leu
1               5                   10                  15

Thr Ala Trp Ala Gln Ala Thr Ala Lys Thr Phe Thr Asn Pro Leu Ser
            20                  25                  30

Pro Leu Ser Leu Val Pro Gly Ala Pro Arg Leu Ala Ala Gly Tyr Glu
        35                  40                  45

Leu Leu Tyr Arg Leu Gly Lys Glu Tyr Glu Lys Pro Ala Phe Asp Ile
 50                  55                  60

Lys Ser Val Arg Ser Asn Gly Arg Asp Ile Pro Ile Val Glu Gln Thr
 65                  70                  75                  80

Val Leu Glu Lys Pro Phe Cys Lys Leu Val Arg Phe Lys Arg Tyr Ala
                 85                  90                  95

Asp Asp Pro Glu Thr Ile Lys Leu Leu Lys Asp Glu Pro Val Val Leu
                100                 105                 110

Val Ala Ala Pro Leu Ser Gly His His Ala Thr Leu Leu Arg Asp Thr
            115                 120                 125

Val Arg Thr Leu Leu Gln Asp His Lys Val Tyr Val Thr Asp Trp Ile
130                 135                 140

Asp Ala Arg Met Val Pro Val Glu Glu Gly Ala Phe His Leu Ser Asp
145                 150                 155                 160

Tyr Ile Tyr Tyr Ile Gln Glu Phe Ile Arg His Ile Gly Ala Glu Asn
                165                 170                 175

Leu His Val Ile Ser Val Cys Gln Pro Thr Val Pro Val Leu Ala Ala
            180                 185                 190

Ile Ser Leu Met Ala Ser Ala Gly Glu Lys Thr Pro Arg Thr Met Thr
            195                 200                 205

Met Met Gly Gly Pro Ile Asp Ala Arg Lys Ser Pro Thr Ala Val Asn
210                 215                 220

Ser Leu Ala Thr Asn Lys Ser Phe Glu Trp Phe Glu Asn Asn Val Ile
225                 230                 235                 240

Tyr Thr Val Pro Ala Asn Tyr Pro Gly His Gly Arg Arg Val Tyr Pro
                245                 250                 255

Gly Phe Leu Gln His Ala Gly Phe Val Ala Met Asn Pro Asp Arg His
            260                 265                 270

Leu Ser Ser His Tyr Asp Phe Tyr Leu Ser Leu Val Glu Gly Asp Ala
            275                 280                 285

Asp Asp Ala Glu Ala His Val Arg Phe Tyr Asp Glu Tyr Asn Ala Val
290                 295                 300

Leu Asp Met Ala Ala Glu Tyr Tyr Leu Asp Thr Ile Arg Glu Val Phe
305                 310                 315                 320

Gln Glu Phe Arg Leu Ala Asn Gly Thr Trp Ala Ile Asp Gly Asn Pro
                325                 330                 335

Val Arg Pro Gln Asp Ile Lys Ser Thr Ala Leu Met Thr Val Glu Gly
            340                 345                 350

Glu Leu Asp Asp Ile Ser Gly Ala Gly Gln Thr Ala Ala Ala His Asp
            355                 360                 365

Leu Cys Ala Gly Ile Pro Lys Ile Arg Lys Gln His Leu Asn Ala Ala
370                 375                 380

His Cys Gly His Tyr Gly Ile Phe Ser Gly Arg Arg Trp Arg Glu Glu
385                 390                 395                 400

Ile Tyr Pro Gln Leu Arg Asp Phe Ile Arg Lys Tyr His Gln Ala Ser
                405                 410                 415

Ala Thr Arg

<210> SEQ ID NO 18
<211> LENGTH: 1260
<212> TYPE: DNA
<213> ORGANISM: Cupriavidus necator

<400> SEQUENCE: 18

```
atgcatattg cggctcgcaa gaaccagaat agcggggacc gagccatgct gtaccacgcc    60
taccagatct acgcggacat gatactgccg gcctgcacgc tggcggagct ggctgccgcg   120
acgctggcgg caaatcccag gtccggtggt ttcgacgcgg tgccccgcct gcgtgccgcc   180
tgcgagctca tcgcactggt gcggctcacg caccaccggc cggccttcgg catcgaccac   240
gcaaccgtcg gcggccagcc ggtgccggtc accgaggaag tcgtcgcgcg cacgccgttc   300
tgctcgctgc tgcacttccg ccgccacggc atcgtcggcc agccgcgcgt gctgctggtg   360
gcgccgatgt ccggccactt cgccacgctg ctgcgcggca cggtccagac catgctggcc   420
gaccacgacg tctatctcac cgactggcac aaccccgcg acattccgtt gctggccggg    480
cgcttcggct tcgatgaatt cgtgcagcac ctgatcggct tcctgcagac gctgggcgga   540
ggcacgcatc tggtggcgat tgccagcct gccgtggcag cgctggcggc agcggcactc   600
atggccgagg acggggatcc cgcccagccg cccagcctga cgctgatggc cggccccatc   660
gacgcgcgcg tcaatccgac caaggtcaac gcgctggcca tgagccaacc cctcgaatgg   720
ttcgagcgca ccttgatcgg catggtgccg ctgcgctttg ccggcgcgat gcggcgcgtc   780
tacccgggcc acgtgcagct gctggccttc atgagcatga acccggagcg gcacgaacag   840
gcgctgcgcg agctctacgc cctgcgcgag gcgggcgagc acgacaaggc cgatgccatc   900
cgcgacttct acatcgagta cttcgccacc atggacctga ccgcggagtt ctacctggaa   960
accgtcagcc tggtattcca gcgcttcctg ctggcccagg gctgcttga cgtgagcgga  1020
cgccgtgtcc gcacgcgcgc catccaccgc accgccctgc tcaccgtgga gggtgaacgc  1080
gacgatatct cgccatcgg ccagaccgtg cggcgcagg acctgtgctc cagcctgcgc   1140
ccctacatgc gcatgcatca tgtgcagacc ggggtcgggc actatggcgt gttcaacggc  1200
aggcggtggg agacgcaggt gtaccgctg gtgcgcaaca ccatctacac cagcagctaa  1260
```

<210> SEQ ID NO 19
<211> LENGTH: 419
<212> TYPE: PRT
<213> ORGANISM: Cupriavidus necator

<400> SEQUENCE: 19

```
Met His Ile Ala Ala Arg Lys Asn Gln Asn Ser Gly Asp Arg Ala Met
1               5                   10                  15

Leu Tyr His Ala Tyr Gln Ile Tyr Ala Asp Met Ile Leu Pro Ala Cys
            20                  25                  30

Thr Leu Ala Glu Leu Ala Ala Ala Thr Leu Ala Ala Asn Pro Arg Ser
        35                  40                  45

Gly Gly Phe Asp Ala Val Pro Arg Leu Arg Ala Ala Cys Glu Leu Ile
    50                  55                  60

Ala Leu Val Arg Leu Thr His His Arg Pro Ala Phe Gly Ile Asp His
65                  70                  75                  80

Ala Thr Val Gly Gly Gln Pro Val Pro Val Thr Glu Glu Val Val Ala
                85                  90                  95

Arg Thr Pro Phe Cys Ser Leu Leu His Phe Arg Arg His Gly Ile Val
            100                 105                 110

Gly Gln Pro Arg Val Leu Leu Val Ala Pro Met Ser Gly His Phe Ala
        115                 120                 125

Thr Leu Leu Arg Gly Thr Val Gln Thr Met Leu Ala Asp His Asp Val
    130                 135                 140

Tyr Leu Thr Asp Trp His Asn Pro Arg Asp Ile Pro Leu Leu Ala Gly
145                 150                 155                 160
```

```
Arg Phe Gly Phe Asp Glu Phe Val Gln His Leu Ile Gly Phe Leu Gln
                165                 170                 175

Thr Leu Gly Gly Gly Thr His Leu Val Ala Ile Cys Gln Pro Ala Val
                180                 185                 190

Ala Ala Leu Ala Ala Ala Ala Leu Met Ala Glu Asp Gly Asp Pro Ala
                195                 200                 205

Gln Pro Pro Ser Leu Thr Leu Met Ala Gly Pro Ile Asp Ala Arg Val
            210                 215                 220

Asn Pro Thr Lys Val Asn Ala Leu Ala Met Ser Gln Pro Leu Glu Trp
225                 230                 235                 240

Phe Glu Arg Thr Leu Ile Gly Met Val Pro Leu Arg Phe Ala Gly Ala
                245                 250                 255

Met Arg Arg Val Tyr Pro Gly His Val Gln Leu Leu Ala Phe Met Ser
                260                 265                 270

Met Asn Pro Glu Arg His Glu Gln Ala Leu Arg Glu Leu Tyr Ala Leu
            275                 280                 285

Arg Glu Arg Gly Glu His Asp Lys Ala Asp Ala Ile Arg Asp Phe Tyr
            290                 295                 300

Ile Glu Tyr Phe Ala Thr Met Asp Leu Thr Ala Glu Phe Tyr Leu Glu
305                 310                 315                 320

Thr Val Ser Leu Val Phe Gln Arg Phe Leu Leu Ala Gln Gly Leu Leu
                325                 330                 335

Asp Val Ser Gly Arg Arg Val Arg Thr Arg Ala Ile His Arg Thr Ala
                340                 345                 350

Leu Leu Thr Val Glu Gly Glu Arg Asp Asp Ile Cys Ala Ile Gly Gln
            355                 360                 365

Thr Val Ala Ala Gln Asp Leu Cys Ser Ser Leu Arg Pro Tyr Met Arg
            370                 375                 380

Met His His Val Gln Thr Gly Val Gly His Tyr Gly Val Phe Asn Gly
385                 390                 395                 400

Arg Arg Trp Glu Thr Gln Val Tyr Pro Leu Val Arg Asn Thr Ile Tyr
                405                 410                 415

Thr Ser Ser
```

HIGH MOLECULAR WEIGHT PHA-PRODUCING MICROBE AND METHOD OF PRODUCING HIGH MOLECULAR WEIGHT PHA USING SAME

TECHNICAL FIELD

The present invention relates to a technique to produce a biodegradable polyhydroxyalkanoate with a higher molecular weight by a polyhydroxyalkanoate (hereinafter, referred to as PHA)-producing microorganism. More specifically, the present invention relates to a method for producing a high molecular weight PHA by a microorganism with a disruption in a gene for a PHA degrading enzyme.

BACKGROUND ART

Polyhydroxyalkanoates are polyester-type organic polymers produced by various microorganisms. Actually, PHAs are biodegradable thermoplastic polymers and also producible from renewable resources. Hence, some attempts have been made to industrially produce a PHA as an environmentally friendly material or biocompatible material for various industrial applications.

PHAs consist of units of monomers generally called hydroxyalkanoic acids which are specifically exemplified by 3-hydroxybutyric acid, 3-hydroxyvaleric acid, 3-hydroxyhexanoic acid, 3-hydroxyoctanoic acid, other 3-hydroxyalkanoic acids with a longer alkyl chain, and 4-hydroxybutyric acid. The polymer molecules are formed by homopolymerization or copolymerization of these hydroxyalkanoic acids.

Examples of PHAs include poly-3-hydroxybutyric acid (hereinafter abbreviated as P(3HB)) which is a homopolymer of 3-hydroxybutyric acid (hereinafter abbreviated as 3HB); a copolymer of 3HB and 3-hydroxyvaleric acid (hereinafter abbreviated as 3HV) (hereinafter, the copolymer is abbreviated as P(3HB-co-3HV)); and a copolymer of 3HB and 3-hydroxyhexanoic acid (hereinafter abbreviated as 3HH) (hereinafter, the copolymer is abbreviated as P(3HB-co-3HH)). Other examples include a copolymer of 3HB and 4-hydroxybutyric acid (hereinafter abbreviated as 4HB) (hereinafter, the copolymer is abbreviated as P(3HB-co-4HB)).

The properties of PHAs are dependent on the molecular weight. PHAs having as high a molecular weight as possible are preferred for fiber processing. Thus, the development of techniques to control the molecular weight of PHAs, particularly to increase the molecular weight of PHAs, in a fermentative production process is essential to achieve use of PHAs in industrial applications.

As described below, several techniques for controlling the molecular weight of PHAs have been reported.

Non Patent Literatures 1, 2, and 3 teach a production method for P(3HB) with a weight average molecular weight of higher than 10,000,000 by culturing *Escherichia coli* cells into which has been introduced *Ralstonia eutropha*-derived genes involved in PHA synthesis while controlling the pH and glucose concentration. These references show that high molecular weight P(3HB) has better physical properties (e.g., tensile strength and restretchability) which are important for fiber processing or others.

Patent Literature 1 shows that in production of P(3HB) using *Escherichia coli* cells harboring an expression vector that contains a PHA synthase gene whose expression is under control of an inducible promoter, enzyme expression regulation by varying the amount of inducer enables control of the weight average molecular weight between 780,000 and 4,000,000.

Patent Literature 2 shows that expression of a PHA synthase gene integrated into a bacterial chromosome results in PHAs that have variable molecular weights depending on the integration site. In the case where an *Aeromonas caviae*-derived PHA synthase gene and genes for supplying substrate monomers were integrated into the *Ralstonia eutropha* chromosome, PHA copolymers including 3-hydroxyhexanoate and 3-hydroxyoctanoate which have a molecular weight of 400,000 to 10,000,000 were accumulated.

There are also some study reports on control of the molecular weight of P(3HB-co-3HH).

Patent Literature 3 discloses a technique to produce P(3HB-co-3HH) with a weight average molecular weight of 5,100,000 by culturing *Ralstonia eutropha* cells into which has been introduced *Escherichia coli*-derived 3-ketoacyl ACP reductase gene (fabG) which encodes an enzyme involved in PHA production, in the presence of a vegetable oil as a carbon source.

As mentioned above, several techniques to control the molecular weight of PHAs, such as control of culture conditions and the activity of PHA synthases and introduction of a gene involved in PHA synthesis, have been reported.

Non Patent Literature 4 shows that *C. necator* has at least 9 PHA degrading enzymes. Although some study reports on microorganisms with disruptions in any of the genes for these PHA degrading enzymes have been published, what are revealed by these reports are enzyme features and decomposition and utilization of accumulated PHAs, and the influence of disruption on the molecular weight of PHAs is unknown. For example, Non Patent Literature 5 shows that disruption of the phaZ1 gene (which has the base sequence of SEQ ID NO:16, and encodes an amino acid sequence of SEQ ID NO:17) or the phaZ2 gene (which has the base sequence of SEQ ID NO:18, and encodes the amino acid sequence of SEQ ID NO:19) is associated with reduced decomposition of P(3HB) accumulated in *C. necator* cells.

As for the phaZd gene (phaZ6 gene), which is a member of the PHA degrading enzyme gene family, Non Patent Literature 6 shows that disruption of this gene does not affect decomposition and utilization of PHAs. Thus, how the phaZ6 gene works in cells is unknown.

CITATION LIST

Patent Literature

Patent Literature 1: U.S. Pat. No. 5,811,272
Patent Literature 2: U.S. Pat. No. 6,593,116
Patent Literature 3: WO 2006/101176

Non Patent Literature

Non Patent Literature 1: Appl. Microbiol. Biotechnol., 47: 140-3 (1997)
Non Patent Literature 2: J. Macromol. Sci., Pure Appl. Chem., A 35: 319-35 (1998)
Non Patent Literature 3: Int. J. Biol. Macromol., 25: 87-94 (1999)
Non Patent Literature 4: Microbiology., 156: 2136-52 (2010)
Non Patent Literature 5: J Bacteriol., 185: 3788-94 (2003)
Non Patent Literature 6: J Bacteriol., 187: 6982-90 (2005)

SUMMARY OF INVENTION

Technical Problem

An object of the present invention is to provide a method for producing a PHA using a microorganism strain capable of accumulating a high molecular weight PHA.

Solution to Problem

The present inventors conducted studies on how to grow microorganisms capable of accumulating high molecular weight PHAs. As a result, they found that disruption of particular PHA degrading enzyme gene (s) of a PHA-producing microorganism, in particular, of *Cupriavidus necator* allows for synthesis of high molecular weight PHAs. The present invention was completed based on this finding.

Specifically, the present invention relates to a method for producing a PHA copolymer which includes culturing a microorganism, wherein at least a portion of either of the following genes (a) and (b) of the microorganism has been altered by substitution, deletion, insertion, and/or addition to reduce or eliminate the activity of a PHA degrading enzyme encoded by the gene:

(a) a PHA degrading enzyme gene encoding the amino acid sequence of SEQ ID NO:2 in the sequence listing; and (b) a gene encoding a polypeptide having at least 85% sequence identity to the amino acid sequence of SEQ ID NO:2 in the sequence listing and having PHA degrading enzyme activity.

Preferably, at least a portion of an additional PHA degrading enzyme gene of the microorganism has also been altered by substitution, deletion, insertion, and/or addition.

The additional PHA degrading enzyme gene is preferably either of the following genes (c) and (d):

(c) a PHA degrading enzyme gene encoding the amino acid sequence of SEQ ID NO:17 and/or a PHA degrading enzyme gene encoding the amino acid sequence of SEQ ID NO: 19 in the Sequence Listing; and (d) a gene encoding a polypeptide having at least 85% sequence identity to the amino acid sequence of SEQ ID NO:17 in the Sequence Listing and having PHA degrading enzyme activity, and/or a gene encoding a polypeptide having at least 85% sequence identity to the amino acid sequence of SEQ ID NO:19 in the Sequence Listing and having PHA degrading enzyme activity.

The microorganism is preferably a microorganism into which has been introduced either of the following genes (e) and (f):

(e) a PHA synthase gene encoding the amino acid sequence of SEQ ID NO:15 in the Sequence Listing; and (f) a gene encoding a polypeptide having at least 85% sequence identity to the amino acid sequence of SEQ ID NO:15 in the Sequence Listing and having PHA synthase activity.

The microorganism is preferably a microorganism belonging to the genus *Cupriavidus*.

The microorganism is preferably *Cupriavidus necator*.

The PHA is preferably a PHA copolymer containing units derived from 3-hydroxyhexanoic acid.

The method preferably includes using a fat/oil having a free fatty acid content of at least 50% as a carbon source.

Preferably, palmitic acid accounts for 40 to 60% of the free fatty acid content.

The present invention further relates to a microorganism, wherein at least a portion of either of the following genes (g) and (h) of the microorganism has been altered by substitution, deletion, insertion, and/or addition to reduce or eliminate the activity of a PHA degrading enzyme encoded by the gene:

(g) a PHA degrading enzyme gene encoding the amino acid sequence of SEQ ID NO:2 in the Sequence Listing; and (h) a gene encoding a polypeptide having at least 85% sequence identity to the amino acid sequence of SEQ ID NO:2 in the Sequence Listing and having PHA degrading enzyme activity, and at least a portion of an additional PHA degrading enzyme gene of the microorganism has also been altered by substitution, deletion, insertion, and/or addition.

The additional PHA degrading enzyme gene is preferably either of the following genes (i) and (j):

(i) a PHA degrading enzyme gene encoding the amino acid sequence of SEQ ID NO:17 and/or a PHA degrading enzyme gene encoding the amino acid sequence of SEQ ID NO: 19 in the Sequence Listing; and (j) a gene encoding a polypeptide having at least 85% sequence identity to the amino acid sequence of SEQ ID NO:17 in the Sequence Listing and having PHA degrading enzyme activity, and/or a gene encoding a polypeptide having at least 85% sequence identity to the amino acid sequence of SEQ ID NO:19 in the Sequence Listing and having PHA degrading enzyme activity.

The microorganism is preferably a microorganism into which has been introduced either of the following genes (k) and (l):

(k) a PHA synthase gene encoding the amino acid sequence of SEQ ID NO:15 in the Sequence Listing; and (l) a gene encoding a polypeptide having at least 85% sequence identity to the amino acid sequence of SEQ ID NO:15 in the Sequence Listing and having PHA synthase activity.

The microorganism is preferably a microorganism belonging to the genus *Cupriavidus*.

The microorganism is preferably *Cupriavidus necator*.

Advantageous Effects of Invention

The present invention makes it possible to produce high molecular weight PHAs, which are industrially useful.

DESCRIPTION OF EMBODIMENTS

The following description is offered to demonstrate the present invention in detail.

One aspect of the present invention is a method for producing a PHA copolymer which includes culturing a microorganism, wherein at least a portion of either of the following genes (a) and (b) of the microorganism has been altered by substitution, deletion, insertion, and/or addition to reduce or eliminate the activity of a PHA degrading enzyme encoded by the gene: (a) a PHA degrading enzyme gene encoding the amino acid sequence of SEQ ID NO:2 in the sequence listing; and (b) a gene encoding a polypeptide having at least 85% sequence identity to the amino acid sequence of SEQ ID NO:2 in the sequence listing and having PHA degrading enzyme activity.

The PHA degrading enzyme gene encoding the amino acid sequence of SEQ ID NO:2 and having the base sequence of SEQ ID NO:1 is called the phaZd gene or phaZ6 gene. An important feature of the present invention is to use a microorganism which has been manipulated to disrupt at least a portion of at least the phaZ6 gene or a gene having physiological functions equivalent to the phaZ6 gene, among existing PHA degrading enzyme genes, by substitution, deletion, insertion, and/or addition. As specifically shown in EXAMPLES below, compared to disruption of only one of the phaZ1 and phaZ2 genes, which are both PHA degrading enzyme genes, disruption of the phaZ6 gene alone or of the phaZ6 gene and an additional PHA degrading enzyme gene of *C. necator* results in PHAs with much higher molecular weight. The present invention is the first to show this fact. Examples of the gene having physiological functions equivalent to the phaZ6 gene include a gene encoding a polypeptide having at least 85% sequence identity to the amino acid sequence of SEQ ID NO:2 in the Sequence Listing and having PHA degrading enzyme activity. The sequence identity to the amino acid sequence of SEQ ID NO:2 in the Sequence Listing is preferably at least 90%, more preferably at least 95% in terms of increasing the likelihood that the gene has physiological functions equivalent to the phaZ6 gene. The sequence identity of the gene to the base sequence of SEQ ID NO:1 in the Sequence Listing is preferably at least 85%, more preferably at least 90%, still more preferably at least 95%.

Alteration of at least a portion of a particular gene by substitution, deletion, insertion, and/or addition can be accomplished by any method known to persons skilled in the art. Typical examples include a method using the mechanisms of transposons and homologous recombination (Ohman et al., J. Bacteriol., 162: 1068-1074 (1985)); a method based on the principles of site-specific integration that can occur as a result of homologous recombination, and elimination that can occur as a result of the second homologous recombination event (Noti et al., Methods Enzymol., 154: 197-217 (1987)); and a method in which the sacB gene derived from *Bacillus subtilis* is allowed to co-exist in a microorganism strain, and then the gene is eliminated by the second homologous recombination event, and thereby the microorganism strain is easily isolated as a strain resistant to a sucrose-added medium (Schweizer, Mol. Microbiol., 6: 1195-1204 (1992), Lenz et al., J. Bacteriol., 176: 4385-4393 (1994)). Any method can be used without particular limitation as long as a target PHA degrading enzyme gene on the chromosome is site-specifically disrupted or deactivated. Specifically, mention may be made of, for example, a method of deleting from the start codon to the stop codon of a target PHA degrading enzyme gene on the chromosome; a method of deleting a portion of the gene sequence from the start codon to the stop codon; a method of introducing the stop codon into the gene sequence; a method of deleting the start codon; and a method of inducing a frameshift mutation by deletion or insertion. A further example is disruption of the promoter of a target PHA degrading enzyme gene, which results in reduced expression of the PHA degrading enzyme.

The phrase "to reduce or eliminate the activity of a PHA degrading enzyme" as used herein means that as a result of alteration of at least a portion of a particular gene by substitution, deletion, insertion, and/or addition, the activity of a PHA degrading enzyme encoded by the PHA degrading enzyme gene is reduced compared to the PHA degrading enzyme activity before the substitution, deletion, insertion, and/or addition, or is completely eliminated, and is not particularly limited as long as a PHA with an increased molecular weight, which is an object of the present invention, is provided. Specifically, the PHA degrading enzyme activity is preferably reduced to 20% or lower, more preferably 15% or lower, still more preferably 10% or lower. Complete elimination of the activity is most preferable. The percentage of reduction of the PHA degrading enzyme activity can be measured by directly measuring the PHA degrading enzyme activity, or alternatively can be estimated based on the effectiveness in suppressing a reduction of the PHA molecular weight by a later-described method for evaluating flask-scale PHA production, for example.

Preferably, at least a portion of an additional PHA degrading enzyme gene of the microorganism used in the present invention has also been altered by substitution, deletion, insertion, and/or addition to reduce or eliminate the activity of a PHA degrading enzyme encoded by the gene. Namely, it is preferable to use a microorganism in which two or more PHA degrading enzyme genes have been altered at least partially by substitution, deletion, insertion, and/or addition in such a manner that the activity of the PHA degrading enzymes encoded by these genes is reduced or eliminated. Examples of the additional PHA degrading enzyme gene include the PHA degrading enzymes mentioned by Steinbuchel et al. (Microbiology., 156: 2136-52 (2010)) including the phaZ1 gene (which encodes the amino acid sequence of SEQ ID NO:17 and has the base sequence of SEQ ID NO:16) and the phaZ2 gene (which encodes the amino acid sequence of SEQ ID NO:19 and has the base sequence of SEQ ID NO:18). The microorganism used in the present invention preferably contains disruptions in the phaZ6 gene and the phaZ1 gene, or in the phaZ6 gene and the phaZ2 gene, more preferably in the phaZ6 gene, the phaZ1 gene, and the phaZ2 gene.

Besides the genes mentioned above, other examples of the additional PHA degrading enzyme gene include a gene having equivalent physiological functions. Mention may be made of, for example, a gene encoding a polypeptide having at least 85% sequence identity to the amino acid sequence of SEQ ID NO:17 or the amino acid sequence of SEQ ID NO: 19 in the Sequence Listing and having PHA degrading enzyme activity. The sequence identity to the amino acid sequence of SEQ ID NO: 17 or the amino acid sequence of SEQ ID NO:19 in the Sequence Listing is preferably at least 90%, more preferably at least 95% in terms of increasing the likelihood that the encoded PHA degrading enzyme has PHA degrading enzyme activity. The sequence identity of the gene to the base sequence of SEQ ID NO:16 or the base sequence of SEQ ID NO:18 in the Sequence Listing is preferably at least 85%, more preferably at least 90%, still more preferably at least 95%. The method for altering at least a portion of the gene by substitution, deletion, insertion, and/or addition is as described above.

The microorganism used in the present invention may be a PHA-synthesizing bacterium containing PHA degrading enzyme genes. Examples include those belonging to the genus *Cupriavidus*. *Cupriavidus necator* strains are preferable among the genus *Cupriavidus*, and in particular, *Cupriavidus necator* H16 is most preferable. Of course, a mutant strain obtainable by artificially mutating the microorganism, and a recombinant strain obtained by mutating the microorganism through genetic engineering can also be used.

The microorganism used in the present invention may be a microorganism obtainable by introducing a PHA synthase gene into a host microorganism. In the case of producing a PHA copolymer containing units derived from 3-hydroxybutyric acid, a microorganism may be used, into which have been introduced appropriately selected genes, such as a gene for the synthesis of units derived from a 3-hydroxyalkanoic acid other than 3-hydroxybutyric acid or of 4-hydroxyalkanoic acid, and/or a gene encoding an enzyme involved in the synthesis of PHAs containing such units. In particular, in the case of producing P(3HB-co-3HH), it is preferable to use a strain into which has been introduced a PHA synthase gene derived from a P(3HB-co-3HH)-producing bacterium, such as *Aeromonas caviae, Aeromonas hydrophila*, or *Chromobacterium* species, or an altered gene thereof. Examples of the PHA synthase gene include, but are not limited to, a PHA synthase encoding the amino acid sequence of SEQ ID NO:15, and a gene encoding a polypeptide having at least 85% sequence identity to the amino acid sequence and having PHA synthase activity. The sequence identity to the amino acid sequence of SEQ ID NO:15 is preferably at least 90%, more preferably at least 95% in terms of ensuring PHA synthase activity.

The PHA produced by the method of the present invention may be any PHA producible by a microorganism, but is preferably a PHA made by polymerization of a composition including at least one 3-hydroxyalkanoic acid selected from C4 to C16 3-hydroxyalkanoic acids, or a PHA copolymer made by copolymerization of a composition including at least one 3-hydroxyalkanoic acid selected from C4 to C16 3-hydroxyalkanoic acids. Specific examples include polyhydroxybutyrate P(3HB) made by polymerization of a C4 3-hydroxyalkanoic acid; poly(3-hydroxybutyrate-co-3-hydroxyhexanoate) P(3HB-co-3HH) made by copolymerization of C4 and C6 3-hydroxyalkanoic acids; poly(3-hydroxybutyrate-co-3-hydroxyvalerate) P(3HB-co-3HV) made by copolymerization of C4 and C5 3-hydroxyalkanoic acids; and polyhydroxyalkanoates (PHAs) made by polymerization or copolymerization of C4 to C14 3-hydroxyalkanoic acids. The type of PHA to be produced can be suitably selected by introducing a known gene involved in PHA synthesis into, for example, *C. necator* used as a host microorganism.

It is observed that disruption of PHA degrading enzyme genes including the phaZ6 gene of *C. necator* is effective in increasing the molecular weight of PHAs containing 3-hydroxybutyric acid. Considering the substrate specificity of the enzyme, the PHA in the present invention is preferably a PHA containing 3-hydroxybutyric acid units, more preferably a PHA copolymer containing 3-hydroxybutyric acid units, among others. The present invention is particularly useful in producing a PHA copolymer containing units derived from 3-hydroxyhexanoic acid in addition to units derived from 3-hydroxybutyric acid, such as P(3HB-co-3HH).

The PHA can be produced by culturing the microorganism by a known method. Any carbon source assimilated by the microorganism can be used, and examples include carbon sources generally used for microorganism culture, such as alcohols, sugars, fats/oils, and/or fatty acids. Preferred are sugars such as glucose, fructose, and sucrose; alcohols such as glycerol; oils/fats such as palm oil, palm kernel oil, corn oil, coconut oil, olive oil, soybean oil, rapeseed oil, and Jatropha oil, and fractionated oils thereof; and fatty acids such as hexanoic acid, octanoic acid, lauric acid, oleic acid, stearic acid, palmitic acid, and myristic acid, and derivatives thereof. Palm kernel olein obtainable as a low melting point fraction from palm kernel oil can be mentioned as a more preferred example, in addition to vegetable oils such as palm oil and palm kernel oil. For the reason of avoiding competitions with food, by-products of fat/oil refining, such as palm oil fatty acid distillate (PFAD), palm kernel oil fatty acid distillate (PKFAD), and rapeseed oil fatty acid distillate, can also be mentioned. In general, the use of a low-cost carbon source such as PFAD tends to result in a PHA with a low molecular weight. By contrast, the method of the present invention can suppress reducing the molecular weight even when PFAD or the like is used as a carbon source.

In the case of using a fatty acid, fat/oil, and/or mixture of these as a carbon source, the fatty acid, fat/oil, and/or mixture of these may be emulsified with a phosphoric acid salt or protein before use. Examples of phosphoric acid salts include orthophosphates such as disodium hydrogen phosphate and potassium dihydrogen phosphate, pyrophosphates such as sodium pyrophosphate, metaphosphates such as sodium hexametaphosphate, and polyphosphates such as sodium polyphosphate. Examples of proteins include lactoproteins, soybean proteins, and products of partial decomposition of gluten, and salts of these. Examples of lactoproteins include casein, sodium caseinate, and whey.

In the case of using a by-product of fat/oil refining as a carbon source, the fat/oil has a free fatty acid content of preferably at least 50%, more preferably at least 80%, still more preferably at least 90%.

The term "free fatty acid" as used herein refers to fatty acids that are not bound to other compounds. Examples of long-chain free fatty acids include caprylic acid, capric acid, lauric acid, myristic acid, palmitic acid, stearic acid, oleic acid, linoleic acid, linolenic acid, arachidic acid, and palmitoleic acid.

Preferably, palmitic acid accounts for 40 to 60%, more preferably 45 to 55% of the free fatty acid content.

The PHA can be accumulated in the microorganism by culturing the microorganism on a PHA-producing medium after the microorganism is proliferated on a preculture medium. The preculture medium is not particularly limited as long as the microorganism is able to proliferate on the medium.

The PHA-producing medium contains a carbon source as described above, and may contain additional ingredients such as a nitrogen source and inorganic salts. Examples of nitrogen sources include ammonia and ammonium salts such as ammonium chloride, ammonium sulfate, and ammonium phosphate. Examples of inorganic salts include potassium dihydrogen phosphate, disodium hydrogen phosphate, magnesium phosphate, magnesium sulfate, and sodium chloride. The medium may further contain an antibiotic (e.g. kanamycin) which corresponds to a drug resistant gene contained in a gene expression plasmid.

The culture temperature may be any temperature at which the microorganism is able to grow, and is preferably 20° C. to 40° C. The culture period is not particularly limited, and may be about 1 day to 10 days.

The PHA produced by the method of the present invention can be collected from cells by a known method. For example, the following method can be used. After culturing the microorganism, cultured cells are separated from the culture medium using a centrifuge or the like, and the cells are washed with distilled water and methanol, and then dried. From the dried cells, the PHA is extracted in an organic solvent such as chloroform. The obtained PHA-containing solution is filtered to remove cell components, and the filtrate is mixed with a poor solvent such as methanol or hexane to cause the PHA to precipitate. The mixture is further filtered or centrifuged to remove the supernatant, and the residue is dried. Thus, the PHA can be collected.

The productivity of microorganism cells can be measured by a known method such as absorptiometry or dry cell weight determination. The yield of the substance produced by the microorganism can be determined by a known method such as GC or HPLC. The PHA content accumulated in the cells can be measured after extracting the PHA from cultured cells in an organic solvent such as chloroform, and drying the extract, in accordance with the method of Kato et al. (Appl. Microbiol. Biotechnol., 45, 363(1996); Bull. Chem. Soc., 69, 515 (1996)).

The term "method for evaluating flask-scale PHA production" as used herein refers to a series of later-described methods for microorganism culturing, PHA extraction, PHA yield evaluation, and PHA weight molecular weight evaluation.

The composition of the seed culture medium is as follows: 1% (w/v) meat-extract, 1% (w/v) Bacto-Trypton, 0.2% (w/v) yeast-extract, 0.9% (w/v) $Na_2HPO_4.12H_2O$, 0.15% (w/v) $KH_2PO_4$.

The composition of the PHA-producing medium is as follows: 1.1% (w/v) $Na_2HPO_4.12H_2O$, 0.19% (w/v) $KH_2PO_4$, 0.13% (w/v) $(NH_4)_2SO_4$, 0.1% (w/v) $MgSO_4.7H_2O$, 0.1% (v/v) trace metal salt solution (a solution of 1.6% (w/v) $FeCl_3.6H_2O$, 1% (w/v) $CaCl_2.2H_2O$, 0.02% (w/v) $CoCl_2.6H_2O$, 0.016% (w/v) $CuSO_4.5H_2O$, and 0.012% (w/v) $NiCl_2.6H_2O$ in 0.1 N hydrochloric acid). The carbon source is a single carbon source of palm kernel-oil olein which is a low melting point fraction of palm kernel oil.

A glycerol stock (50 µL) of the microorganism of interest is inoculated into the seed culture medium (10 mL), and incubated therein for 24 hours. The resulting culture is used as a seed culture.

Culture for PHA production is performed as follows: the seed culture is inoculated into a shake flask containing the PHA-producing medium (50 mL) to a concentration of 1.0% (v/v); and the flask is incubated at 30° C. for 21 to 25 hours with shaking. After incubation, cells are collected by centrifugation, washed with methanol, lyophilized, and measured for dry cell weight.

To the obtained dry cells (1 g) is added chloroform (100 ml). The mixture is stirred at room temperature for one whole day and night, and the PHA in the cells is extracted. The extracted solution is filtered to remove cell residues, and concentrated in an evaporator to a total volume of about 30 ml. To the concentrated solution is gradually added hexane (90 ml), and the mixture is left to stand for one hour with slow stirring. The precipitate of PHA is filtered off, and vacuum-dried at 50° C. for three hours. The dried PHA is weighed, and the PHA yield is calculated.

Next, the molecular weight of the obtained PHA is measured. Gel permeation chromatography is used to analyze the weight average molecular weight of the PHA. The extracted PHA (15 mg) is dissolved in chloroform (10 mL), and the solution is filtered through a 0.2-µm filter to give a measurement sample. An amount of 0.05 ml of the sample is analyzed. The analysis is performed at 40° C. using a measurement system SLC-10A (available from SHIMADZU CORPORATION) and two Shodex GPC K-806L columns (available from Showa Denko K.K.) connected in series. The mobile phase is chloroform (1.0 ml/min), and an RI detector (RID-10A, available from SHIMADZU CORPORATION) is used. Polystyrenes treated in the same manner (available from Showa Denko K.K., weight average molecular weight: about 7,000,000, about 1,070,000, 150,000, 30,000) are used as standard samples, and the weight average molecular weight of the PHA is determined from the calibration curve.

The weight average molecular weight of PHAs produced by the present invention is preferably at least 3,500,000, more preferably at least 4,000,000, as determined by the method for evaluating flask-scale PHA production.

EXAMPLES

The present invention is described in detail below with reference to examples, but the present invention is not limited to these examples. The general gene manipulation can be carried out as described in Molecular Cloning (Cold Spring Harbor Laboratory Press (1989)). Enzymes, cloning hosts and other materials to be used in gene manipulation can be purchased from commercially available suppliers and can be used according to the instructions given by the suppliers. The enzymes are not particularly limited as long as they can be used in gene manipulation.

Preparation 1

Preparation of KNK005 ΔphaZ6

First, a plasmid for gene substitution was prepared. Specifically, the preparation procedure was as follows.

PCR was performed using the chromosomal DNA of *C. necator* H16 as a template and primers 1 and 2 of SEQ ID NOs:3 and 4. The PCR consisted of (1) 98° C. for 2 minutes; and 25 cycles of: (2) 98° C. for 15 seconds, 60° C. for 30 seconds, and 68° C. for 2 minutes. The polymerase used was KOD-plus- (available from TOYOBO CO., LTD.). Subsequently, PCR was performed using primers 3 and 4 of SEQ ID NOs:5 and 6 in the same manner. Using the two DNA fragments obtained by PCR as templates, together with primers 1 and 4, PCR was performed under the same conditions, and the resulting DNA fragment was digested with the restriction enzyme SwaI.

The DNA fragment was ligated to the SwaI-digested vector pNS2X-sacB disclosed in JP 2007-259708 A with a DNA ligase (Ligation High, available from TOYOBO CO., LTD.) to give a plasmid vector for gene disruption pNS2X-phaZ6 (−+) carrying the base sequences upstream and downstream of the phaZ6 structural gene.

Next, cells with a gene disruption were prepared. Specifically, *Escherichia coli* S17-1 (ATCC47055) was transformed with the plasmid vector for gene disruption pNS2X-phaZ6(−+), and cultured with KNK005 (see U.S. Pat. No. 7,384,766) on Nutrient Agar (available from Difco) to allow conjugative transfer. KNK005 is a *Cupriavidus necator* H16-derived strain into which has been introduced a gene encoding a PHA synthase having the amino acid sequence of SEQ ID NO:15 in the Sequence Listing.

The culture was inoculated onto Simmons agar medium containing kanamycin (250 mg/L) (2 g/L sodium citrate, 5 g/L sodium chloride, 0.2 g/L magnesium sulfate heptahydrate, 1 g/L ammonium dihydrogen phosphate, 1 g/L potassium dihydrogen phosphate, 15 g/L agar, pH 6.8), and grown cells on the agar medium were selected, and collected as a strain in which the plasmid had been integrated in the chromosome of *C. necator* H16. The strain was cultured for two generations in Nutrient Broth (available from Difco), and then diluted and plated on a 15% sucrose-containing Nutrient Agar medium. Grown cells were collected as a strain without the plasmid.

Further, PCR analysis was performed to isolate a strain in which from the start codon to the stop codon of the phaZ6 gene on the chromosome had been deleted. This strain with a gene disruption was named KNK005 ΔphaZ6. The obtained strain KNK005 ΔphaZ6 is a strain in which from the start codon to the stop codon of the phaZ6 gene on the chromosome of *Cupriavidus necator* H16 has been deleted, and in which a gene encoding a PHA synthase having the amino acid sequence of SEQ ID NO:15 in the Sequence Listing has been introduced into the chromosome.

Preparation 2

Preparation of KNK005 ΔphaZ1

First, a plasmid for gene substitution was prepared. Specifically, the preparation procedure was as follows.

PCR was performed using the chromosomal DNA of *C. necator* H16 as a template and primers 5 and 6 of SEQ ID NOs:7 and 8. The PCR consisted of (1) 98° C. for 2 minutes; and 25 cycles of: (2) 98° C. for 15 seconds, 60° C. for 30 seconds, and 68° C. for 2 minutes. The polymerase used was KOD-plus- (available from TOYOBO CO., LTD.). Subsequently, PCR was performed using primers 7 and 8 of SEQ ID NOs:9 and 10. Using the two DNA fragments obtained by PCR as templates together with primers 5 and 8, PCR was performed under the same conditions, and the resulting DNA fragment was digested with the restriction enzyme SwaI.

The DNA fragment was ligated to the SwaI-digested vector pNS2X-sacB disclosed in JP 2007-259708 A with a DNA ligase (Ligation High, available from TOYOBO CO., LTD.) to give a plasmid vector for gene disruption pNS2X-phaZ1 (−+) carrying the DNA sequences upstream and downstream of the phaZ1 structural gene.

Following the same procedure as that for preparing a gene disruption strain in Preparation 1 and using KNK005 as a parent strain and pNS2X-phaZ1(−+), a strain (KNK005 ΔphaZ1) with a chromosomal gene disruption in which from the start codon to the stop codon of the phaZ1 gene on the chromosome had been deleted was obtained. The obtained KNK005 ΔphaZ1 is a strain in which from the start codon to the stop codon of the phaZ1 gene on the chromosome of *Cupriavidus necator* H16 has been deleted, and in which a gene encoding a PHA synthase having the amino acid sequence of SEQ ID NO:15 in the Sequence Listing has been introduced into the chromosome.

Preparation 3

Preparation of KNK005 ΔphaZ2

First, a plasmid for gene substitution was prepared. Specifically, the preparation procedure was as follows.

PCR was performed using the chromosomal DNA of *C. necator* H16 as a template and primers 9 and 10 of SEQ ID NOs:11 and 12. The PCR consisted of (1) 98° C. for 2 minutes; and 25 cycles of: (2) 98° C. for 15 seconds, 60° C. for 30 seconds, and 68° C. for 2 minutes. The polymerase used was KOD-plus- (available from TOYOBO CO., LTD.). Subsequently, PCR was performed using primers 11 and 12 of SEQ ID NOs:13 and 14 in the same manner. Using the two DNA fragments obtained by PCR as templates together with primers 9 and 12, PCR was performed under the same conditions, and the resulting DNA fragment was digested with the restriction enzyme SwaI.

The SwaI-digested DNA fragment was ligated to the vector pNS2X-sacB disclosed in JP 2007-259708 A with a DNA ligase (Ligation High, available from TOYOBO CO., LTD.) to give a plasmid vector for gene disruption pNS2X-phaZ2 (−+) carrying the base sequences upstream and downstream of the phaZ2 structural gene.

Following the same procedure as that for preparing a gene disruption strain in Preparation 1 and using KNK005 as a parent strain and pNS2X-phaZ2 (−+), a strain (KNK005 ΔphaZ2) with a chromosomal gene disruption in which from the 16th codon to the stop codon of the phaZ2 gene on the chromosome had been deleted was obtained. The obtained KNK005 ΔphaZ2 is a strain in which from the 16th codon to the stop codon of the phaZ2 gene on the chromosome of *Cupriavidus necator* H16 has been deleted, and in which a gene encoding a PHA synthase having the amino acid sequence of SEQ ID NO:15 in the Sequence Listing has been introduced into the chromosome.

Preparation 4

Preparation of KNK005 ΔphaZ1,6

Following the same procedure as that for preparing a gene disruption strain in Preparation 2 and using KNK005 ΔphaZ6 as a parent strain and pNS2X-phaZ1 (−+), a strain (KNK005 ΔphaZ1,6) with chromosomal gene disruptions in which from the start codon to the stop codon of the phaZ6 gene and from the start codon to the stop codon of phaZ1 gene on the chromosome had been deleted was obtained.

Preparation 5

Preparation of KNK005 ΔphaZ2,6

Following the same procedure as that for preparing a gene disruption strain in Preparation 3 and using KNK005 ΔphaZ6 as a parent strain and pNS2X-phaZ2 (−+), a strain (KNK005 ΔphaZ2,6) with chromosomal gene disruptions in which from the start codon to the stop codon of the phaZ6 gene and from the start codon to the stop codon of the phaZ2 gene on the chromosome had been deleted was obtained.

Example 1

PHA Production by KNK005 ΔphaZ6

The composition of the seed culture medium used was as follows: 1% (w/v) Meat-extract, 1% (w/v) Bacto-Trypton, 0.2% (w/v) Yeast-extract, 0.9% (w/v) $Na_2HPO_4.12H_2O$, 0.15% (w/v) $KH_2PO_4$.

The composition of the PHA-producing medium used was as follows: 1.1% (w/v) $Na_2HPO_4.12H_2O$, 0.19% (w/v) $KH_2PO_4$, 0.13% (w/v) $(NH_4)_2SO_4$, 0.1% (w/v) $MgSO_4.7H_2O$, 0.1% (v/v) trace metal salt solution (a solution of 1.6% (w/v) $FeCl_3.6H_2O$, 1% (w/v) $CaCl_2.2H_2O$, 0.02% (w/v) $CoCl_2.6H_2O$, 0.016% (w/v) $CuSO_4.5H_2O$, and 0.012% (w/v) $NiCl_2.6H_2O$ in 0.1 N hydrochloric acid). The carbon source used was a single carbon source of palm kernel-oil olein which is a low melting point fraction of palm kernel oil.

A glycerol stock (50 µl) of KNK005 ΔphaZ6 prepared in Preparation 1 was inoculated into the seed culture medium (10 ml) and incubated for 24 hours. The culture was used as a seed culture.

Culture for PHA production was performed as follows: the seed culture was inoculated into a shake flask containing the PHA-producing medium (50 mL) to a concentration of 1.0% (v/v); and the flask was incubated at 30° C. for 21 to 25 hours with shaking. After incubation, cells were collected by centrifugation, washed with methanol, lyophilized, and measured for dry cell weight.

To the obtained dry cells (1 g) was added chloroform (100 ml). The mixture was stirred at room temperature for 24 hours, and the PHA in the cells was extracted. The extracted solution was filtered to remove cell residues, and concentrated in an evaporator to a total volume of about 30 ml. To the concentrated solution was gradually added hexane (90 ml), and the mixture was left to stand for one hour with slow stirring. The precipitate of PHA was filtered off, and vacuum-dried at 50° C. for three hours. The dried PHA was weighed, and the PHA yield was calculated. Table 1 shows the results.

Next, the molecular weight of the obtained PHA was measured. Gel permeation chromatography was used to analyze the weight average molecular weight of the PHA. The extracted PHA (15 mg) was dissolved in chloroform (10 mL), and the solution was filtered through a 0.2-μm filter to give a measurement sample. An amount of 0.05 ml of the sample was analyzed. The analysis was performed at 40° C. using a measurement system SLC-10A (available from SHIMADZU CORPORATION) and two Shodex GPC K-806L columns (available from Showa Denko K.K.) connected in series. The mobile phase was chloroform (1.0 ml/min), and an RI detector (RID-10A, available from SHIMADZU CORPORATION) was used. Polystyrenes treated in the same manner (available from Showa Denko K.K., weight average molecular weight: about 7,000,000, about 1,070,000, 150,000, 30,000) were used as standard samples, and the weight average molecular weight of the PHA was determined from the calibration curve. Table 1 shows the results.

Example 2

PHA Production by KNK005 ΔphaZ1,6

Following the same procedure as in Example 1 and replacing KNK005 ΔphaZ6 with KNK005 ΔphaZ1,6 prepared in Preparation 4, a PHA was produced. The yield and weight average molecular weight of the PHA were also determined in the same manner. Table 1 shows the results.

Example 3

PHA Production by KNK005 ΔphaZ2,6

Following the same procedure as in Example 1 and replacing KNK005 ΔphaZ6 with KNK005 ΔphaZ2,6 prepared in Preparation 5, a PHA was produced. The yield and weight average molecular weight of the PHA were also determined in the same manner. Table 1 shows the results.

Comparative Example 1

PHA Production by KNK005 ΔphaZ1

Following the same procedure as in Example 1 and replacing KNK005 ΔphaZ6 with KNK005 ΔphaZ1 prepared in Preparation 2, a
PHA was produced. The yield and weight average molecular weight of the PHA were also determined in the same manner. Table 1 shows the results.

Comparative Example 2

PHA Production by KNK005 ΔphaZ2

Following the same procedure as in Example 1 and replacing KNK005 ΔphaZ6 with KNK005 ΔphaZ2 prepared in Preparation 3, a PHA was produced. The yield and weight average molecular weight of the PHA were also determined in the same manner. Table 1 shows the results.

Comparative Example 3

PHA Production by KNK005

Following the same procedure as in Example 1 and replacing KNK005 ΔphaZ6 with KNK005 without a disruption in the PHA degrading enzyme genes, a PHA was produced. The yield and weight average molecular weight of the PHA were also determined in the same manner. Table 1 shows the results.

The results show that the PHA weight average molecular weight achieved by disruption of the phaZ6 gene in Example 1 was more than double that of Comparative Example 3 using KNK005. In addition, the weight average molecular weight of the PHA of Example 1 was remarkably increased compared to Comparative Examples 1 and 2 in which a PHA degrading enzyme gene other than the phaZ6 gene had been disrupted. Disruption of the phaZ1 or phaZ2 gene in addition to the phaZ6 gene in Examples 2 and 3 resulted in PHA weight average molecular weights of 3,500,000 or more, in particular, the use of KNK005 ΔphaZ1,6 in Example 2 resulted in a weight average molecular weight of 4,000,000 or more.

TABLE 1

| | Strain | PHA yield (g/L) | Weight average molecular weight ($\times 10^4$) |
|---|---|---|---|
| Example 1 | KNK005 ΔphaZ6 | 5.1 | 340 |
| Example 2 | KNK005 ΔphaZ1, 6 | 3.7 | 421 |
| Example 3 | KNK005 ΔphaZ2, 6 | 4.2 | 385 |
| Comparative Example 1 | KNK005 ΔphaZ1 | 3.9 | 209 |
| Comparative Example 2 | KNK005 ΔphaZ2 | 3.3 | 200 |
| Comparative Example 3 | KNK005 | 4.6 | 166 |

Example 4

Composition Analysis of PHAs

The composition of the PHAs produced by the transformants was analyzed by gas chromatography. Each of the dried PHAs (20 mg) was mixed with a sulfuric acid/methanol mixture (15:85, 2 mL) and chloroform (2 mL), and the system was hermetically sealed. The mixture was heated at 100° C. for 140 minutes, so that the PHA was decomposed to methyl ester. The methyl ester was cooled, and sodium hydrogen carbonate (1.5 g) was gradually added to the cooled methyl ester for neutralization. This mixture was left to stand until carbon dioxide gas production stopped. To the mixture was added diisopropyl ether (4 mL), and the resulting mixture was stirred thoroughly, followed by centrifugation. The monomer unit composition of the PHA decomposition product in the supernatant was determined by capillary gas chromatography. The gas chromatograph was GC-17A available from SHIMADZU CORPORATION, and the capillary column was NEUTRA BOND-1 available from GL Sciences Inc. (column length: 25 m, column inner diameter: 0.25 mm, liquid membrane thickness: 0.4 μm). The carrier gas was helium, the column inlet pressure was 100 kPa, and the sample was used in an amount of 1 μl. The temperature was increased from an initial temperature of 100° C. to 100° C. at 8° C./min, and further increased from 200° C. to 290° C. at 30° C./min.

The analysis performed under the above-mentioned conditions revealed that the PHAs produced by the transformants KNK005, KNK005 ΔphaZ6, KNK005 ΔphaZ1, KNK005 ΔphaZ2, KNK005 ΔphaZ1,6, and KNK005 ΔphaZ2,6 into which had been introduced a PHA synthase gene encoding a PHA synthase having the amino acid sequence of SEQ ID NO:15 were all P(3HB-co-3HH).

Example 5

PHA Production by KNK005 ΔphaZ6 in Jar Fermenter with PFAD as Carbon Source

The composition of the seed culture medium was as follows: 1% (w/v) Meat-extract, 1% (w/v) Bacto-Trypton, 0.2% (w/v) Yeast-extract, 0.9% (w/v) $Na_2HPO_4.12H_2O$, 0.15% (w/v) $KH_2PO_4$.

The composition of the preculture medium was as follows: 1.1% (w/v) $Na_2HPO_4.12H_2O$, 0.19% (w/v) $KH_2PO_4$, 1.29% (w/v) $(NH_4)_2SO_4$, 0.1% (w/v) $MgSO_4.7H_2O$, 2.5% (w/v) palm W oleic oil, 0.5% (v/v) trace metal salt solution (a solution of 1.6% (w/v) $FeCl_3.6H_2O$, 1% (w/v) $CaCl_2.2H_2O$, 0.02% (w/v) $CoCl_2.6H_2O$, 0.016% (w/v) $CuSO_4.5H_2O$, and 0.012% (w/v) $NiCl_2.6H_2O$ in 0.1 N hydrochloric acid).

The composition of the PHA-producing medium was as follows: 0.578% (w/v) $Na_2HPO_4.12H_2O$, 0.101% (w/v) $KH_2PO_4$, 0.437% (w/v) $(NH_4)_2SO_4$, 0.15% (w/v) $MgSO_4.7H_2O$, 0.75% (v/v) trace metal salt solution (a solution of 1.6% (w/v) $FeCl_3.6H_2O$, 1% (w/v) $CaCl_2.2H_2O$, 0.02% (w/v) $CoCl_2.6H_2O$, 0.016% (w/v) $CuSO_4.5H_2O$, and 0.012% (w/v) $NiCl_2.6H_2O$ in 0.1 N hydrochloric acid). The carbon source was palm fatty acid distillate (PFAD) (available from MALAYSIAN BIOTECHNOLOGY CORPORATION SDN BDH; free fatty acid content 95.0%; fatty acid composition C12:0 0.2%, C14:0 1.2% C16:0 47.6%, C16:1 0.3%, C18:1 35.7%, C18:2 9.7%, C18:3 0.4%, C20:0 0.4%; melting point 43.8° C.) which was emulsified in a manner described below before use.

PFAD (550 g) and water (450 g) were weighed out, and individually heated to 60° C. In the water were dissolved $Na_2HPO_4.12H_2O$ (4.7 g) and sodium caseinate (2.75 g). After they were dissolved, the solution was combined with PFAD, and the mixture was pre-emulsified with a homomixer (LABORATORY MIXER EMULSIFIER, available from SILVERSON) at a stirring rate of 2500 rpm. The resulting emulsion was further emulsified with a high-pressure homogenizer (model: PANDA2K, available from GEA Niro Soavi) at a pressure of 10 bar to provide an emulsion.

A glycerol stock (50 μl) of KNK005 ΔphaZ6 prepared in Preparation 1 was inoculated into the seed culture medium (10 ml), and incubated for 24 hours, and then inoculated to a concentration of 1.0% (v/v) into a 3-L jar fermenter (MDL-300, available from B. E. Marubishi Co., Ltd.) containing the preculture medium (1.8 L). The fermenter was incubated for 28 hours under the following operating conditions: culture temperature of 30° C., stirring rate of 500 rpm, aeration rate of 1.8 L/min, and pH controlled in the range of 6.7 to 6.8. The pH was controlled using a 7% aqueous ammonium hydroxide solution.

Culture for PHA production was performed as follows. The seed culture was inoculated to a concentration of 25% (v/v) into a 10-L jar fermenter (MDL-1000, available from B. E. Marubishi Co., Ltd.) containing the production medium (2 L). The fermenter was incubated under the following operating conditions: culture temperature of 32° C., stirring rate of 450 rpm, and aeration rate 3.0 L/min, and pH controlled in the range of 6.7 to 6.8. The pH was controlled using a 7% ammonium hydroxide aqueous solution. The incubation was continued for 45 to 54 hours, and the culture broth was sampled during and at the end of incubation. The samples were centrifuged to collect cells, and the cells were washed with methanol, lyophilized, and measured for dry cell weight. The yield and weight average molecular weight of the PHA were also determined in the same manner as in Example 1. Table 2 shows the results.

Example 6

PHA Production by KNK005 ΔphaZ1,6 Using PFAD as Carbon Source

Following the same procedure as in Example 5 and replacing KNK005 ΔphaZ6 with KNK005 ΔphaZ1,6 prepared in Preparation 4, a PHA was produced. The yield and weight average molecular weight of the PHA were also measured in the same manner. Table 2 shows the results.

Preparation 6

Preparation of KNK005 ΔphaZ1,2,6

Following the same procedure as in Preparation 2 and using KNK005 ΔphaZ2,6 as a parent strain and pNS2X-phaZ1 (−+), a strain (KNK005 ΔphaZ1,2,6) with chromosomal gene disruptions in which from the start codon to the stop codon of the phaZ2 gene, from the start codon to the stop codon of the phaZ6 gene, and from the start codon to the stop codon of the phaZ1 gene on the chromosome had been deleted was prepared.

Example 7

PHA Production by KNK005 ΔphaZ1,2,6 in Jar Fermenter Using PFAD as Carbon Source Following the same procedure as in Example 5 and replacing KNK005 ΔphaZ6 with KNK005 ΔphaZ1,2,6 prepared in Preparation 6, a PHA was produced. The yield and weight average molecular weight of the PHA were also determined in the same manner. Table 2 shows the results.

Comparative Example 4

PHA Production by KNK005 in Jar Fermenter Using PFAD as Carbon Source

Following the same procedure as in Example 5 and replacing KNK005 ΔphaZ6 with KNK005 without a disruption in the PHA degrading enzyme genes, a PHA was produced. The yield and weight average molecular weight of the PHA were also determined in the same manner. Table 2 shows the results.

Table 2 shows the yield and weight average molecular weight analyzed approximately 45 hours from the start of incubation. The results show that KNK005 ΔphaZ6 improved the weight average molecular weight compared to KNK005. It is revealed that KNK005 ΔphaZ1,6 is more effective in improving the weight average molecular weight, and KNK005 ΔphaZ1,2,6 is still more effective in improving the weight average molecular weight.

TABLE 2

| Strain | | Culture period (Hrs) | PHA yield (g/L) | Weight average molecular weight (×10⁴) |
|---|---|---|---|---|
| Example 5 | KNK005 ΔphaZ6 | 45 | 121 | 166 |
| Example 6 | KNK005 ΔphaZ1, 6 | 45 | 120 | 188 |
| Example 7 | KNK005 ΔphaZ1, 2, 6 | 43 | 136 | 203 |
| Comparative Example 4 | KNK005 | 45 | 114 | 156 |

Example 8

Composition Analysis of PHAs

The composition of the PHAs was analyzed in the manner described in Example 4. The results confirm that the PHAs synthesized by the transformants KNK005, KNK005 ΔphaZ6, KNK005 ΔphaZ1,6, and KNK005 ΔphaZ1,2,6 into which had been introduced a PHA synthase gene encoding a PHA synthase having the amino acid sequence of SEQ ID NO:15 were all P(3HB-co-3HH).

The invention claimed is:

1. A method for producing a polyhydroxyalkanoate (PHA) copolymer having an increased weight average molecular weight, comprising:
   (1) culturing a PHA producing microorganism,
   wherein at least a portion of a gene encoding a PHA degrading enzyme of the microorganism has been altered by at least one of substitution, deletion, insertion, and addition, to reduce or eliminate an activity of the PHA degrading enzyme,
   wherein the PHA degrading enzyme has
   (a) the amino acid sequence of SEQ ID NO:2, or
   (b) an amino acid sequence having at least 90% sequence identity to the amino acid sequence of SEQ ID NO:2 and has a PHA degrading enzyme activity,
   wherein the microorganism belongs to the genus *Cupriavidus*, and
   (2) producing the PHA copolymer,
   wherein the weight average molecular weight of the produced PHA copolymer is increased compared to the weight average molecular weight of the produced PHA copolymer in a microorganism wherein the gene encoding the PHA degrading enzyme has not been altered, and
   wherein the produced PHA copolymer comprises at least two different type of units selected from the group consisting of 3-hydroxyhexanoic acid (3HH), 3-hydroxybutyric acid (3HB), 3-hydroxyvaleric acid (3HV), 3-hydroxyoctanoic acid (3HO), 4-hydroxybutyric acid (4HB), and a combination thereof.

2. The method according to claim 1, wherein at least a portion of a gene encoding an additional PHA degrading enzyme of the microorganism has been altered by at least one of substitution, deletion, insertion, and addition.

3. The method according to claim 2, wherein the additional PHA degrading enzyme has
   (c) the amino acid sequence of SEQ ID NO:17, or
   (d) an amino acid sequence having at least 90% sequence identity to the amino acid sequence of SEQ ID NO:17 and has a PHA degrading enzyme activity.

4. The method according to claim 1, wherein the microorganism further comprises:
   (e) a gene encoding a PHA synthase having the amino acid sequence of SEQ ID NO:15, or (f) a gene encoding a polypeptide having at least 90% sequence identity to the amino acid sequence of SEQ ID NO:15 and having a PHA synthase activity.

5. The method according to claim 1, wherein the microorganism is *Cupriavidus necator*.

6. The method according to claim 1, wherein the produced PHA copolymer comprises units derived from 3-hydroxyhexanoic acid.

7. The method according to claim 1, wherein the culturing comprises culturing the microorganism in the presence of a carbon source which comprises a free fatty acid at a content of at least 50% based on the total content of fat and oil.

8. The method according to claim 7, wherein the free fatty acid comprises from 40 to 60% of palmitic acid based on the total content of the free fatty acid.

9. The method according to claim 1, wherein the produced PHA copolymer has a weight average molecular weight of at least $340 \times 10^4$.

10. The method according to claim 1, wherein the produced PHA copolymer is purified.

11. The method according to claim 1, wherein a degradation activity of the PHA degrading enzyme in the microorganism is reduced to 10% or lower.

12. The method according to claim 1, wherein the produced PHA copolymer is a P(3HB-co-3HH) copolymer, a P(3HB-co-3HV) copolymer, or a P(3HB-co-4HB) copolymer.

13. The method according to claim 2, wherein the additional PHA degrading enzyme has
(g) the amino acid sequence of SEQ ID NO: 19, or
(h) an amino acid sequence having at least 90% sequence identity to the amino acid sequence of SEQ NO: 19 and has a PHA degrading enzyme activity.

14. The method according to claim 3, wherein at least a portion of a gene encoding a PHA degrading enzyme of the microorganism has been altered by at least one of a substitution, deletion, insertion, and addition, wherein the PHA degrading enzyme has
(i) the amino acid sequence of SEQ ID NO: 19, or
(j) an amino acid sequence having at least 90% sequence identity to the amino acid sequence of SEQ NO: 19 and has a PHA degrading enzyme activity.

15. The method according to claim 1, wherein the produced PHA copolymer comprises units derived from 3-hydroxybutyric acid.

16. A method for producing a polyhydroxyalkanoate (PHA) copolymer having an increased weight average molecular weight, the method comprising:
(1) culturing a PHA producing microorganism, wherein the microorganism belongs to the genus *Cupriavidus* and in which a PHA synthase comprising the amino acid sequence of SEQ ID NO:15 has been introduced, wherein
(a) a phaZ6 gene and a phaZ1 gene on the chromosome of *Cupriavidus* have been deleted;
(b) a phaZ6 gene and a phaZ2 gene on the chromosome of *Cupriavidus* have been deleted; or
(c) a phaZ6 gene, a phaZ1 gene, and a phaZ2 gene on the chromosome of *Cupriavidus* have been deleted; and
(2) producing the PHA copolymer,
wherein the produced PHA copolymer comprises at least two different type of units selected from the group consisting of 3-hydroxyhexanoic acid (3HH), 3-hydroxybutyric acid (3HB), 3-hydroxyvaleric acid (3HV), 3-hydroxyoctanoic acid (3HO), 4-hydroxybutyric acid (4HB), and a combination thereof; and
wherein the weight average molecular weight of the produced PHA copolymer is increased compared to the weight average molecular weight of the produced PHA copolymer in a *Cupriavidus* microorganism wherein the gene encoding the PHA degrading enzyme has not been altered.

17. The method according to claim 16, wherein the produced PHA copolymer is a P(3HB-co-3HH) copolymer, a P(3HB-co-3HV) copolymer, or a P(3HB-co-4HB) copolymer.

* * * * *